United States Patent [19]

Sasson et al.

[11] Patent Number: 4,479,015
[45] Date of Patent: Oct. 23, 1984

[54] PROCESS FOR THE MANUFACTURE OF NITROPHENETOLES

[75] Inventors: Yoel Sasson; Shmuel Zbaida, both of Jerusalem, Israel

[73] Assignee: GADOT, Petrochemical Industries, Ltd., Haifa, Israel

[21] Appl. No.: 456,521

[22] Filed: Jan. 7, 1983

[30] Foreign Application Priority Data

Mar. 3, 1982 [IL] Israel ................................. 65154

[51] Int. Cl.$^3$ ..................... C07C 79/35; C07C 41/16
[52] U.S. Cl. ................................................... 568/584
[58] Field of Search ................................... 568/584

[56] References Cited

FOREIGN PATENT DOCUMENTS 1539183 1/1979 United Kingdom ................ 568/584

Primary Examiner—Bernard Helfin
Attorney, Agent, or Firm—Bacon & Thomas

[57] ABSTRACT

The present invention relates to a process for the manufacture of ortho - or para-nitrophenetole. According to the invention, the respective nitrochlorobenzene is reacted with ethanol and alkali hydroxide in the presence of a catalyst system which comprises a tetramethylammonium salt of a general formula $(CH_3)_4NX$, wherein X is $Cl^-$, $Br^-$, $HSO_4^-$ or $OC_2H_5$, and an aqueous phase. The process has several advantages such as high yields and purity, the products obtained being completely free of side reaction products such as azoxy compounds.

9 Claims, No Drawings

PROCESS FOR THE MANUFACTURE OF NITROPHENETOLES

The present invention relates to an improved process for the ethoxylation of substituted benzene compounds. More particularly, the invention relates to an improved process for the ethoxylation of ortho or para chlor nitro benzene, producing ortho or para nitro phenetole in a substantially pure form.

Para nitrophenetole is an important starting material for various organic synthesis. One of the main uses of para nitrophenetole, on an industrial scale, is in the manufacture of para phenetidine, an important intermediate compound useful in the manufacture of phenacetin, phenocoll, p-phenetylurea and various dyestuff intermediates. Para nitrophenetole is also the starting material in the manufacture of ethoxyquin which is a valuable antioxidant reagent.

The known method for the manufacture of para-nitrophenetole is by ethoxylation of para-nitrochlorobenzene in the presence of ethanol and alkalies, according to the following reaction:

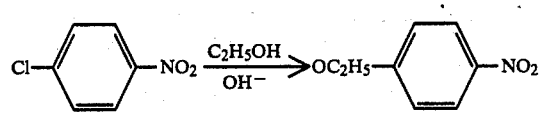

One of the main disadvantages of the method, is the occurence of side reactions and particularly the formation of azoxy compounds according to the following reaction (2):

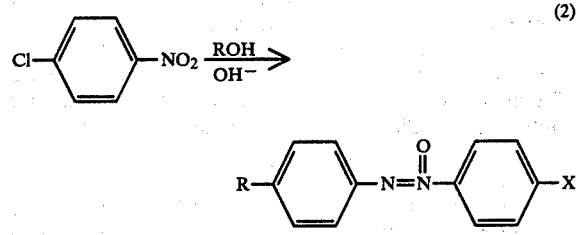

wherein X=Cl, OH, OR.

The literature is quite abundant with various methods to suppress the occurence of reaction (2). These methods can be divided in two main groups: (a) The performance of the reaction, in the presence of air or other oxidants such as described in: U.S. Pat. Nos. 3,085,113 and 3,132,180 J.Org.Chem. 45, 2265, 1980 and C.A. 52, 16294g and (b) the performance of the reaction in the presence of metal oxides such as MnO$_2$; Cu$_2$O; CuCl; CuSO$_4$; Co$_3$O$_4$ etc., as described in Pharmazie 24, 419, 1969 and C.A. 75, 63297 W. The yields reported for the methods using the above additives are in the range of 80–90%. Of course that the incorporation of the metal oxides, requires an additional step for their removal from the reaction product. Furthermore, a main disadvantage is the fact that small amounts of the co-products according to reaction (2) above, will still be formed and will require a recrystallization or distillation step in order to obtain the pure nitrophenetole.

From the above preamble it appears therefore, that is will be a long felt need in the art for a simple process for the manufacture of pure ortho or para-nitrophenetole and does not require the known obsolete method for removal the metal oxide catalyst from reaction system.

Thus, it is one object of the present invention to provide a simple process for the manufacture of pure nitro phenetole (ortho or para). It is another object of the present invention to provide a simple process for the manufacture of pure nitro phenetole (ortho or para) at high yields which does not require further purification. Thus, the invention consists of a process for the manufacture of substantially pure ortho or para nitrophenetole from the respective nitrochlorobenzene, ethanol and alkali hydroxide, being characterized by carrying out the process in a two phase catalytic reaction system which comprises tetramethylammonium salts having the formula (CH$_3$)$_4$NX, wherein X is Cl$^-$, Br$^{-1}$, HSO$_4^-$, or OC$_2$H$_5$, and an aqueous phase. It was found that by carrying out the reaction between the nitrochlorobenzene, ethanol and alkali hydroxide in said two-phase catalytic system, substantially pure ortho or para-nitrophenetole product can be obtained which is completely free from any side reaction products of the azoxy types. In this way, the corresponding nitrophenetole product could be directly processed in a subsequent step, such as hydrogenation for the manufacture of ortho or para phenetidine product without any purification step. It seems that by utilizing a catalytic two phase system for the reaction involved according to the present invention, which requires organic and inorganic constituents, an intimate contact between the reagents is obtained which enables yielding the desired product at very high yields completely free of side reaction products. A similar approach was indeed considered in the past, when a polar aprotic solvent such as dimethylformamide was utilized as a reaction medium. The explanation given for such a solvent, was that it removes the phase barrier due to its dissolution power towards the ionic and organic reactants. Generally, these aprotic solvents are characterized by their high boiling points and due to their high solvent power for the organic moiety, it will be most difficult to remove them from the product by distillation or washing. An elegant solution for these types of reactions was suggested about ten years ago (J.Am.Chem.Soc. 1971, 93, 195) when the so called phase-transfer catalysts was suggested. Examples of such phase transfer catalysts are: tetrabutyl ammonium bromide; trioctyl methyl ammonium bromide; tetrabutyl ammonium sulphate; cetyltrimethyl ammonium bromide; methyltricapryl ammonium bromide etc. One of the characteristic requirements of these types of catalysts, (as mentioned therein) is to possess a sufficient lypophilic property in order to be able to pull the anions into the organic phase.

A comprehensive process on phase transfer catalysis involving heterogeneous reactions was claimed in the U.S. Pat. No. 3,992,432. According to this patent, the reaction between the organic phase and the aqueous phase is conducted in the presence of an organic quaternary salt phase transfer catalyst which is mentioned that transfers a functional reactant ion or group from one phase to another phase. The quaternary salt is defined by (R, R$_2$, R$_3$, R$_4$, M)$^+$ X$^-$ wherein M is nitrogen, arsenic, phosphorus, antimony and bismuth, X is a halide or hydroxy ion and R, R$_2$, R$_3$ and R$_4$ are monovalent hydrocarbon radicals having a total sum of 18 to 70 carbon atoms.

Based on the same principle of phase transfer catalysis, a general process for the manufacture of aromatic ethers was claimed in the U.K. Pat. No. 1,539,183. According to this patent, a water immiscible activated aromatic compound is reacted with an organic hydroxy compound in the presence of aqueous alkali and a phase transfer catalyst. The preferred phase transfer catalysts are defined as quaternary ammonium compounds having a total number of carbon atoms above ten and especially preferred being between 16 and 40 carbon atoms. The reaction between para-chloronitrobenzene with ethanol and sodium hydroxide using cetyl trimethylammonium bromide is also illustrated (Example 6 in said patent). However as specified therein, the yield of para-nitrophenetole obtained is 90% along with 10% of dichloroazoxybenzene. Of course, the presence of so large amounts of by-products will require an additional step of crystallization in order to obtain the pure para nitrophenetole. It is indeed very questionable whether the use of the phase transfer catalyst yielding a high percentage of by-product, is justified particularly considering the costs of the relatively high amounts of catalyst employed in the process.

Tetramethyl ammonium salts although belong to the group of the quarternary ammonium compounds, are specifically excluded from the phase transfer catalyst compounds, in view of their insufficiency lipophylic property which is absolutely required for these compounds (Chemtech May 1981, page 318). It was unexpectedly found that by carrying out the reaction according to the present invention in the presence of tetramethyl ammonium salts such as tetramethyl ammonium bromide, -chloride, -bisulfate, pure nitrophenetole is obtained without any azoxy by-products. It is beyond the scope of the present patent specification to provide a theoretical explanation why the reaction does yield about 10% azoxy compounds in the presence of a phase transfer catalyst—as described in the U.K. Pat. No. 1,539,183—while in the presence of tetra methyl ammonium salts no such by-products are produced.

Among the tetramethyl ammonium salts, the preferred to be utilized in the process according to the present invention are the tetramethyl ammonium chloride and bromide salts which are commercially available in bulk. One may conceive also to utilize other salts of tetramethyl ammonium: $(CH_3)_4NOR$ wherein R might be selected from methyl, propyl, butyl, phenol, benzyl etc. However in this case the phenetole product will also contain small amounts of the respective nitro phenetyl salt.

The aqueous alkali hydroxide may be selected from sodium or potassium hydroxide or mixtures thereof. Generally, sodium hydroxide solutions will be preferred, mainly in view of their lower cost. The concentration may be in a broad range of between 25— to 100% by wt., but concentrated solutions in the range of 40 to 80% by weight are most preferable.

The entire process is very simple to be conducted, the temperature being in the range of 40° to 80° C. At temperature above 80° C., some azoxy compounds start to occur and therefore it would be most desirable not to surpass said upper limit temperature. The amount of catalyst is in the range of 1 to 4% by weight of the reactants. Generally the alcohol and the alkali hydroxide solutions introduced in the reaction will be in excess over the stoichiometrical amounts, but they are not lost in the process being recycled after the removal of the product. The excess of reagents used, can also serve as a good medium for the reaction. According to another embodiment it is possible to use an inert polar solvent for the reaction such as dioxane. In this case, the excess of reactants or the inert solvent will be distilled out and recycled to the process.

The alcohol and the alkali solution may be introduced either entirely at the start of the reaction, or in portions along its proceeding. The latter procedure is indeed preferred, since in this way the reaction will be more moderated and a better control can be done to avoid an increase in temperature above 80° C., thus limiting the chances of side reaction occurence.

The reaction is carried out generally at atmospheric pressure, although vacuum can also be employed, in which case there is a clear advantage of performing the reaction under reflux at lower temperatures, in the range of 60°–70° C., which again will avoid the azoxy formation.

Another advantage of the process according to the present invention, is the very high yields of the product which is above 97% and even above 98% based on the chloronitrobenzene introduced. The only impurity present in the phenetole product, is the starting chloronitrobenzene which does not interfere in the subsequent step of hydrogenation being transformed into aniline which can be easily separated from the phenetidine. This of course is another clear advantage, since according to the known methods, azoxy compounds are formed and difficulties are encountered in their separation from the product.

While the invention has been described in connection with specific embodiments thereof, it will be understood that it is capable of further modifications, and this patent is intended to cover any variation, uses or adaptations of the invention and including such departures from the present disclosure as come within known or customary practice in the art to which the invention pertains and as may be applied to the essential features hereinbefore set forth and as fall within the scope of the invention. In order to further illustrate the nature of this invention and the manner of practising it, the following Examples are presented for clearness of understanding only and no limitation should be understood therefrom.

EXAMPLE 1

In a steel vessel provided with a stirrer and heating elements, an amount of 157 g of 4-nitrochlorobenzene was introduced together with 4 g of tetramethyl ammoniumchloride and 46 g ethanol and vigorously mixed at a temperature of about 68° C. To the mixture, a solution of 320 g of sodium hydroxide (50% by weight concentration) was introduced during 8 hours while the vigorous agitation was continued. After about 3 hours from the sodium hydroxide incorporation, the reaction started and an additional amount of 23 g ethanol was introduced. The mixing continued for an additional period of about four hours after the introduction of the sodium hydroxide solution. The organic phase was separated and the excess of ethanol was evaporated.

The crude product obtained amounted 163 g and its purity, as determined by gas chromatography, was 98% 4-nitrophenetole and 2% of unreacted 4-nitrochlorobenzene.

EXAMPLE 2

In this experiment, the reaction was carried out which the same reagents as in Example 1, using the same amounts, but a vacuum of 500 mm Hg was applied so that the temperature during reflux of the reaction mixture was only 70° C. The product yielded also 163 g, its purity being the same as in Example 1.

EXAMPLE 3

The experiment as described in Example 1 was repeated, but instead of the 4-nitrochlorobenzene, an amount of 157 g 2-nitrochlorobenzene was utilized. The reaction conditions and the other reagents were the same as in Example 1. The product consisted of 160 g of 2-nitrophenetole with a purity of 97% (determined by gas chromatography) and 3% of unreacted 2-chloronitro benzene.

EXAMPLE 4

The experiment as described in Example 1 was repeated but in this case an amount of 100 ml of dioxane as solvent was present which was evaporated at the completion of the process. The crude product contained 160 g of 96% 4-nitrophenetole and 4% of 4-nitrochlorobenzene.

EXAMPLE 5

In a steel vessel provided with a stirrer and heating elements, an amount of 314 g of 4-nitrochlorobenzene was introduced together with 10 g of tetramethyl ammoniumbromide and 92 g ethanol and vigorously mixed at a temperature of about 68° C. To the mixture obtained, a solution of 640 g of sodium hydroxide (50% by wt. concentration) was introduced during about 8 hours while the vigorous agitation was continued. After about 3 hours from the sodium hydroxide addition, a new portion of 46 g ethanol was added and the mixing continued for another period of four hours after the sodium hydroxide incorporation. The organic phase was separated and the excess of ethanol was evaporated. The crude product obtained amounted to 320 g and its purity, as determined by gas chromatography, was 97% 4-nitrophenetole and 3% unreacted 4-nitrochlorobenzene.

EXAMPLE 6

The experiment described in Example 1 was repeated but an amount of 240 g sodium hydroxide (50% by wt concentration) was utilized instead of 320 g in said Example. The product obtained at an amount of 163 g, had the same purity as in Example 1.

EXAMPLE 7

In the same reaction as in Example 1 the following reagents were introduced: 157 g of 4-nitrochlorobenzene, 4 g of tetramethylammonium-chloride and 69 g of ethanol. A vigorous agitation was applied the temperature being kept at 60° C. To the resulting mixture, an amount of 70 g solid sodium hydroxide was added in portions of about 5 g each 30 minutes. After the addition of all the sodium hydroxide the mixture was further agitated at 60° C. for an additional period of 4 hours. To the mixture obtained an amount of 200 ml of toluene were added and two distinct phases were separated. The upper phase contained 163.5 g of 4-nitrophenetole with a purity of 98% as determined by gas chromatography.

We claim:

1. A process for the manufacture of substantially pure nitro-phenetole (ortho or para) from the respective nitrochlorobenzene, ethanol and solid alkali hydroxide, comprising reacting said reactants in a two phase catalytic reaction system which comprises an organic phase and a solid phase in a substantial absence of water, in the presence of a tetramethylammonium salt having the formula $(CH_3)_4NX$, wherein X is $Cl^{-1}$, $Br^-$, $HSO_4^-$ or $OC_2H_5$.

2. A process according to claim 1, wherein the ethanol and alkali hydroxide are used in excess over the stoichiometrical required based on the nitrochlorobenzene.

3. A process according to claim 1, wherein the ethanol and alkali hydroxide are added in portions as the reaction proceeds.

4. A process according to claim 1, wherein said alkali hydroxide is selected from sodium hydroxide, potassium hydroxide and mixtures thereof.

5. A process according to claim 1, wherein an inert polar solvent is present during the reaction.

6. A process according to claim 5, wherein said solvent is dioxane.

7. A process according to claim 1, carried out at atmospheric pressure.

8. A process according to claim 7, carried out at a temperature in the range of 60° to 80° C.

9. A process according to claim 1, carried out under vacuum.

* * * * *